(12) United States Patent
Lu (10) Patent No.: US 11,779,333 B2
(45) Date of Patent: Oct. 10, 2023

(54) DRIVING SWITCHING MECHANISM FOR STAPLING INSTRUMENT AND STAPLING INSTRUMENT

(71) Applicant: SUZHOU BEINUO MEDICAL INSTRUMENTS CO., LTD., Suzhou (CN)

(72) Inventor: Jian Lu, Suzhou (CN)

(73) Assignee: SUZHOU BEINUO MEDICAL INSTRUMENTS CO., LTD., Suzhou (CN)

( * ) Notice: Subject to any disclaimer, the term of this patent is extended or adjusted under 35 U.S.C. 154(b) by 102 days.

(21) Appl. No.: 17/614,537

(22) PCT Filed: Sep. 9, 2020

(86) PCT No.: PCT/CN2020/114281
§ 371 (c)(1),
(2) Date: Nov. 28, 2021

(87) PCT Pub. No.: WO2022/021545
PCT Pub. Date: Feb. 3, 2022

(65) Prior Publication Data
US 2022/0313251 A1    Oct. 6, 2022

(30) Foreign Application Priority Data

Jul. 27, 2020 (CN) .......................... 202010732474.0

(51) Int. Cl.
*A61B 17/072* (2006.01)
*A61B 17/3209* (2006.01)

(52) U.S. Cl.
CPC ........ *A61B 17/072* (2013.01); *A61B 17/3209* (2013.01); *A61B 2017/07285* (2013.01)

(58) Field of Classification Search
CPC ................... A61B 17/072; A61B 2017/07285
See application file for complete search history.

(56) References Cited

U.S. PATENT DOCUMENTS 5,318,221 A * 6/1994 Green .............. A61B 17/07207
227/19
5,465,895 A * 11/1995 Knodel ............ A61B 17/07207
227/176.1
(Continued)

FOREIGN PATENT DOCUMENTS

| CN | 101317780 A | 12/2008 |
| CN | 204708913 A | 10/2015 |

(Continued)

*Primary Examiner* — Gloria R Weeks
(74) *Attorney, Agent, or Firm* — SZDC LAW P.C.

(57) ABSTRACT

This application provides a driving switching mechanism for a stapling instrument. An actuation driving assembly includes a driving sleeve for driving an end effector to perform a closing action and a knife bar driving rod for driving the end effector to perform a stapling action. A handle driving assembly includes a driving handle and a knife bar driving assembly which includes a knife driving member and a handle driving connecting member. The handle driving connecting member is connected to a handle driving portion. The knife driving member is movably connected to the handle driving connecting member, and is movable relative to the handle driving connecting member to a driving position or a driving disengagement position. When the knife driving member is in the driving position, the knife driving member and the knife bar driving rod are engaged as the handle driving portion moves toward a second position.

9 Claims, 6 Drawing Sheets

(56) References Cited

U.S. PATENT DOCUMENTS

| | | | | |
|---|---|---|---|---|
| 6,241,139 | B1 * | 6/2001 | Milliman | A61B 17/068 227/176.1 |
| 7,905,380 | B2 * | 3/2011 | Shelton, IV | A61B 17/07207 227/176.1 |
| 11,179,158 | B2 * | 11/2021 | Chen | A61B 17/1155 |
| 2006/0000867 | A1 * | 1/2006 | Shelton, IV | A61B 17/07207 227/19 |
| 2008/0083806 | A1 * | 4/2008 | Scirica | A61B 17/00234 227/175.1 |
| 2019/0000525 | A1 * | 1/2019 | Messerly | A61B 17/07207 |
| 2019/0307448 | A1 | 10/2019 | Scheib et al. | |

FOREIGN PATENT DOCUMENTS

| | | |
|---|---|---|
| CN | 105935305 A | 9/2016 |
| CN | 106618655 A | 5/2017 |
| CN | 209269765 A | 8/2019 |

\* cited by examiner

DRIVING SWITCHING MECHANISM FOR STAPLING INSTRUMENT AND STAPLING INSTRUMENT

This application is the National Stage Application of PCT/CN2020/114281, filed on Sep. 9, 2020, which claims priority to Chinese Patent Application No. 202010732474.0, filed on Jul. 27, 2020, which is incorporated by reference for all purposes as if fully set forth herein.

FIELD OF THE INVENTION

The present invention relates to a medical device, and more particularly to a driving switching mechanism for a stapling instrument and a stapling instrument.

DESCRIPTION OF THE RELATED ART

An intraluminal stapling instrument may usually include two elongated jaw members. The two jaw members are separately used for gripping or clamping tissue. In some surgical stapling instruments, one of the jaw members carries a staple cartridge which houses a plurality of staples arranged in at least two lateral rows while the other jaw member has an anvil that defines a surface for forming the staple legs as the staples are driven from the staple cartridge. A stapling operation is effected by cam members that travel longitudinally through the staple cartridge, with the cam members acting upon staple pushers to sequentially eject the staples from the staple cartridge. A knife can travel between the staple rows to longitudinally cut and/or open the stapled tissue between the staple rows. For example, the U.S. Pat. No. 6,241,139 discloses a stapling apparatus, with the repeated movement of a handle, jaws can be closed and cutting and stitching operations can be effected.

However, for the structure of stapling instrument that uses a single handle to effect repeated operations of an end effector in the prior art, a large number of complex transmission mechanisms are usually required. As a result, the manufacturing is difficult, the assembly is complex, and an assembly error tends to occur, leading to a fault in the stapling instrument. Therefore, a driving switching structure that can simply and effectively achieve a plurality of operations of stapling instruments is required to resolve the foregoing problem.

SUMMARY OF THE INVENTION

To resolve the foregoing technical problem, a technical solution of the present invention is implemented as follows:

In the technical solution of this application, a driving switching mechanism for a stapling instrument is provided, the stapling instrument includes an end effector and a connecting tube, where the driving switching mechanism includes an actuation driving assembly and a handle driving assembly, and the actuation driving assembly is at least partially disposed inside the connecting tube;

the actuation driving assembly includes a driving sleeve and a knife bar driving rod, the driving sleeve is used for driving the end effector to perform a closing action, and the knife bar driving rod is used for driving the end effector to perform a stapling action;

the handle driving assembly includes a driving handle and a knife bar driving assembly, the driving handle includes a handle driving portion, and the handle driving portion is movable from a proximal first position to a distal second position; and the driving sleeve is at least partially located on a movement path of the handle driving portion; and the knife bar driving assembly includes a knife driving member and a handle driving connecting member, the handle driving connecting member is connected to the handle driving portion, and the knife driving member is movably connected to the handle driving connecting member, and is movable relative to the handle driving connecting member to a driving position or a driving disengagement position; and when the knife driving member is in the driving position, the knife driving member and the knife bar driving rod are engaged during the handle driving portion moving toward the second position.

Preferably, the driving handle further includes a handle holding portion and a handle hinge portion, and the driving handle is rotatably connected to a handle housing by the handle hinge portion.

Further, the driving handle and the handle housing are provided with a first elastic reset member.

Preferably, the knife bar driving assembly further includes a switching control member and a pusher limit member, the switching control member is rotatably connected to a handle housing, the pusher limit member is synchronously rotatably connected to the switching control member, when the switching control member is in an upper position, the pusher limit member abuttingly limits the knife driving member in the driving disengagement position, and when the switching control member is in a lower position, the knife driving member is not limited by the pusher limit member in the driving position.

Preferably, the driving sleeve includes a handle contact portion and a switching limit step; and the handle driving portion pushes the handle contact portion to push the driving sleeve from an initial position to a closed position;

when the driving sleeve is in the initial position, an upper step surface of the switching limit step is in contact with the switching control member, to limit the switching control member in the upper position; and when the driving sleeve is in the closed position, a lower step surface of the switching limit step is in contact with the switching control member, to limit the switching control member in the lower position.

Further, when the driving sleeve is in the closed position, an end of the switching control member further abuts against a lateral step surface of the switching limit step.

Preferably, an end, close to the end effector, of the driving sleeve abuts against an end of a second elastic reset member, and the other end of the second elastic reset member is relatively fastened to the handle housing.

Preferably, the switching control member is further connected to a reset button, and the reset button is at least partially located on an outer side of the handle housing.

Preferably, the knife bar driving rod includes a pusher step and a receding groove, the handle driving connecting member passes through the receding groove to be connected to the knife driving member, a width of the knife driving member is greater than that of the receding groove, and when the knife driving member is in the driving position, the knife driving member and the pusher step of the knife bar driving rod are engaged during the handle driving portion moving toward the second position.

In another aspect, this application further provides a stapling instrument, including an end effector, a connecting tube, and the driving switching mechanism described above.

By means of the foregoing technical solution, the present invention has the following advantages as compared with the prior art:

(1) A knife driving member with a switchable position only requires simple linkage coordination to perform different actions during handle driving.

(2) In coordination with a switching control member, operations of gripping and stapling can be successfully completed by repeatedly driving a handle without actively switching positions of the knife driving member.

(3) With a second elastic reset member, after a stapling instrument completes gripping, the stability of gripping can be kept without loosening.

(4) A pusher step and a receding groove are disposed on a knife bar driving rod, so that space inside a handle housing of the stapling instrument can be effectively utilized, and the function of action switching can be accurately implemented without causing interference between parts.

DETAILED DESCRIPTION OF THE PREFERRED EMBODIMENTS

The following clearly and completely describes the technical solutions in the embodiments of this application with reference to the accompanying drawings in the embodiments of this application. Apparently, the described embodiments are only some embodiments of this application rather than all the embodiments. All other embodiments obtained by persons of ordinary skill in the art based on the embodiments of this application without creative efforts fall within the protection scope of this application.

In this application, according to use description of a device, a proximal end is close to an operator, and a distal end is far away from the operator.

Embodiment

As shown in FIG. 1 to FIG. 8, in this embodiment, stapling instrument for endoscopic surgery is described. The stapling instrument includes an end effector 4 and a connecting tube 5, and a driving switching mechanism for a stapling instrument.

Figure 1:
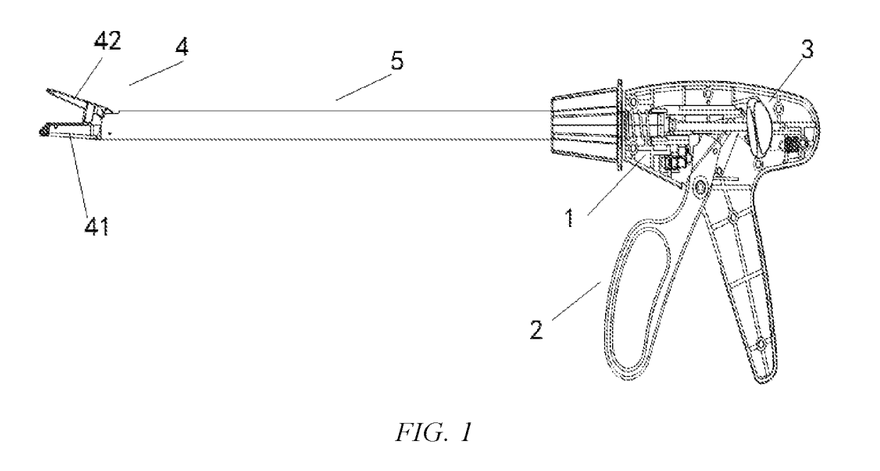
FIG. 1 is a schematic structural diagram of a stapling instrument according to an embodiment of this application.

The end effector 4 of the stapling instrument is used for cutting and stitching tissue after entering a channel in endoscopic surgery. The end effector 4 is provided with a first gripping member 41 and a second gripping member 42. The end effector 4 is connected to a handle apparatus by the connecting tube 5. The first gripping member 41 and the connecting tube 5 are fastened relative to each other. The second gripping member 42 and the connecting tube 5 are rotatable relative to each other. A cartridge is disposed on the first gripping member 41 or the second gripping member 42. A handle driving portion 21 is movable from a first position at a proximal end to a second position at a distal end, to drive the first gripping member 41 and the second gripping member 42 of the end effector 4 to perform gripping or drive the cartridge to implement a stapling action. In this embodiment, gripping and stapling are performed by using the same handle.

Figure 2:
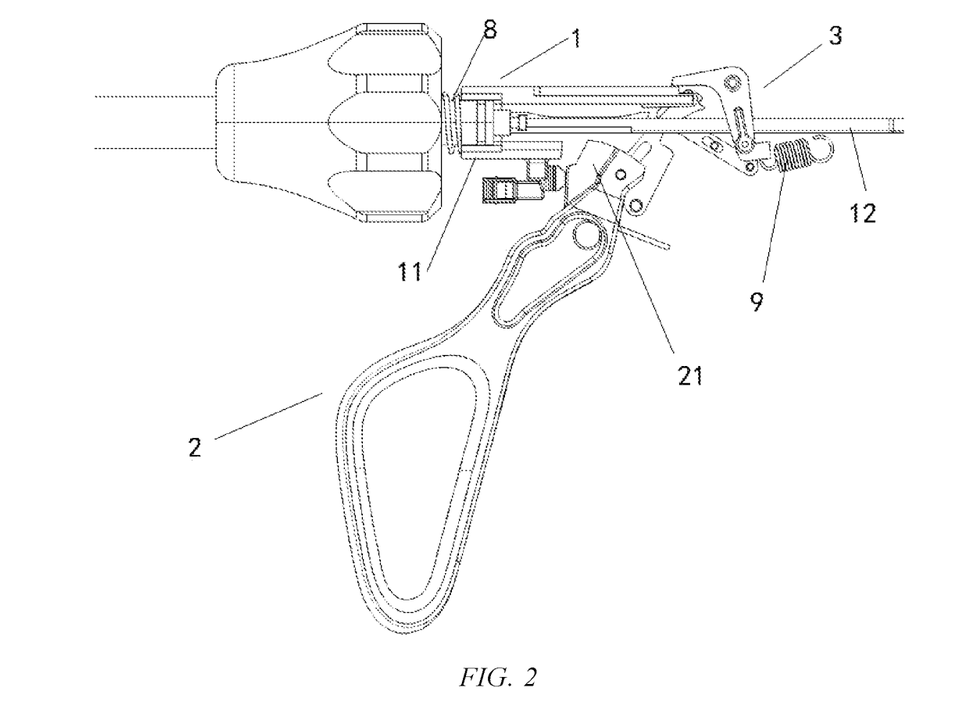
FIG. 2 is a schematic structural diagram of a coordination relationship of a driving switching mechanism according to an embodiment of this application.

Specifically, in this embodiment, the driving switching mechanism includes an actuation driving assembly 1 and a handle driving assembly. The actuation driving assembly 1 is at least partially disposed inside the connecting tube 5. The actuation driving assembly 1 includes a driving sleeve 11 and a knife bar driving rod 12. The driving sleeve 11 is used for driving the end effector 4 to perform a closing action. The knife bar driving rod 12 is used for driving the end effector 4 to perform a stapling action. The handle driving assembly receives a driving force provided by an operator, to transfer the driving force to the actuation driving assembly 1, to implement interaction between the operator and the end actuator.

Figure 3:
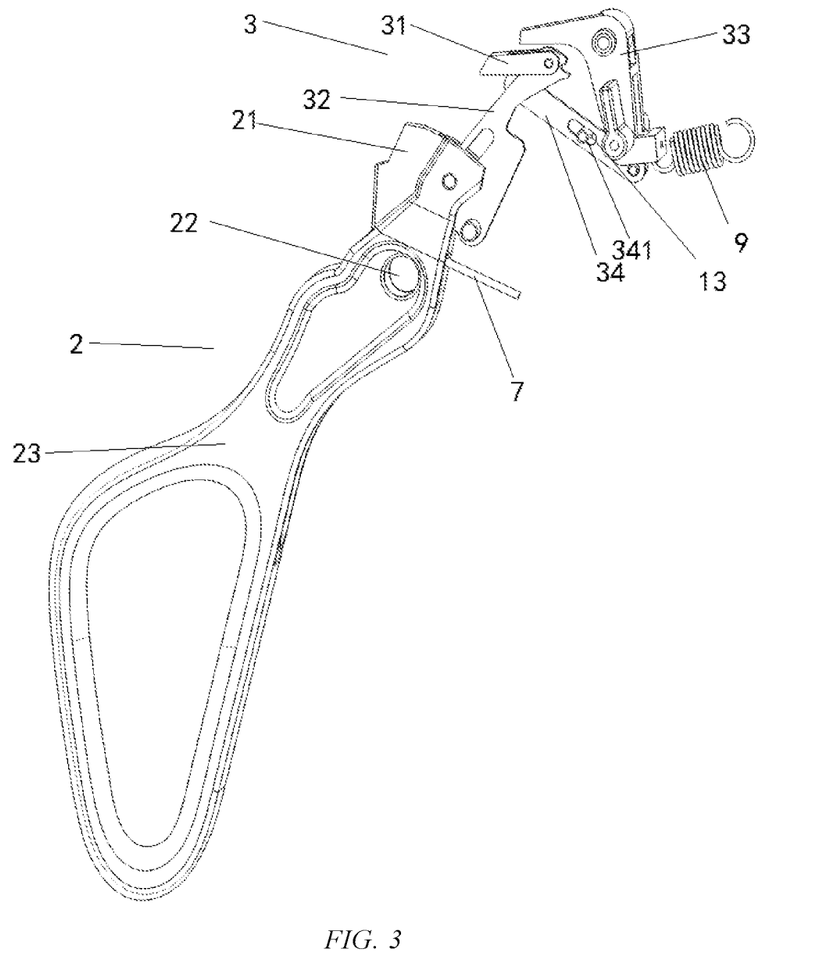
FIG. 3 is a schematic structural diagram of a knife bar driving assembly according to an embodiment of this application.

In this embodiment, because the handle driving assembly can switch states to implement linkage between different parts in the actuation driving assembly 1, the same handle may be pressed to implement different execution actions of the end actuator, that is, separately perform gripping and stapling. Specifically, the handle driving assembly includes a driving handle 2 and a knife bar driving assembly 3. The driving handle 2 includes the handle driving portion 21. The handle driving portion 21 is movable from the first position at the proximal end to the second position at the distal end. The driving sleeve 11 is at least partially located on a movement path of the handle driving portion 21. The knife bar driving assembly 3 includes a knife driving member 31 and a handle driving connecting member 32. The handle driving connecting member 32 is connected to the handle driving portion 21. The knife driving member 31 is movably connected to the handle driving connecting member 32, and is movable relative to the handle driving connecting member 32 to a driving position or a driving disengagement position. When the knife driving member 31 is in the driving position, the knife driving member 31 and the knife bar driving rod 12 are engaged as the handle driving portion 21 moves toward the second position.

To facilitate pressing of the handle, the driving handle 2 further includes a handle holding portion 23 and a handle hinge portion 24. The driving handle 2 is rotatably connected to a handle housing 6 by the handle hinge portion 24. The driving handle 2 and the handle housing 6 are provided with a first elastic reset member. Therefore, every time after the driving handle 2 is pressed, the driving handle 2 can return to an original position. That is, every time the handle driving portion 21 is correspondingly driven to the second position, the handle driving portion 21 automatically returns to the first position. In this embodiment, the first elastic reset member is specifically a coil spring 7.

The knife driving member 31 is specifically rotatably connected to the handle driving connecting member 32, and is therefore separately rotatable to the relatively low driving position or the relative high driving disengagement position. In this embodiment, to automatically implement switching between two positions of the knife driving member 31, the knife bar driving assembly 3 further includes a switching control member 33 and a pusher limit member 34. The switching control member 33 is rotatably connected to a handle housing 6. The pusher limit member 34 is synchronously rotatably connected to the switching control member 33. When the switching control member 33 is in an upper position, the pusher limit member 34 abuttingly limits the knife driving member 31 in the driving disengagement position. When the switching control member 33 is in a lower position, the knife driving member 31 is not limited by the pusher limit member 34 in the driving position. In addition, in this embodiment, the pusher limit member 34 is further provided with a guide chute 341. The rotation of the pusher limit member 34 can be guided and limited in coordination with a fastening guide pin 13 fixed on the housing.

In other embodiments, a linkage mechanism in another manner or an electrical control mechanism may be used to implement position switching of the knife driving member 31, which both fall within the scope of protection of this application.

Figure 5:
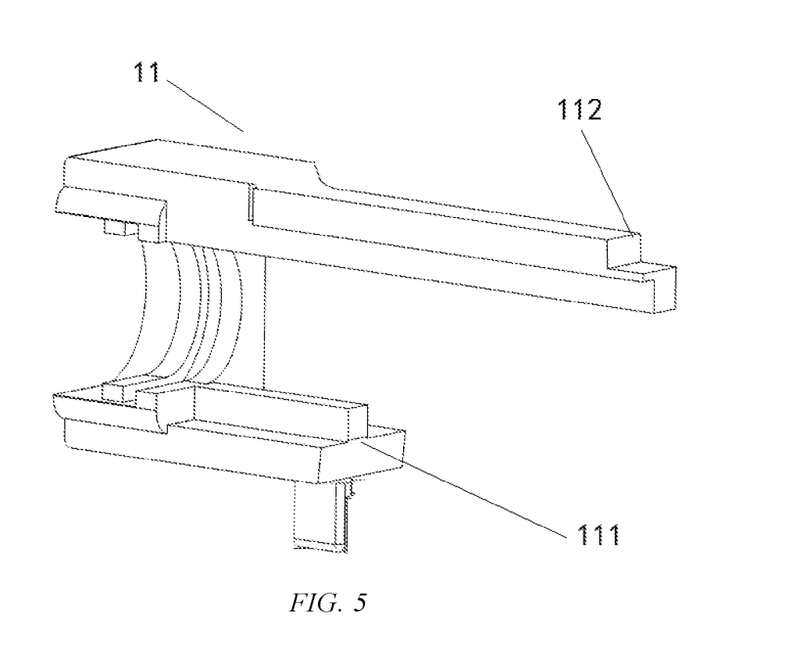
FIG. 5 is a schematic structural diagram of a driving sleeve according to an embodiment of this application.

Further, the driving sleeve 11 includes a handle contact portion 111 and a switching limit step 112. The handle driving portion 21 pushes the handle contact portion 111 to push the driving sleeve 11 from an initial position to a closed position. When the driving sleeve 11 is in the initial position, an upper step surface of the switching limit step 112 is in contact with the switching control member 33, to limit the switching control member 33 in the upper position. When the driving sleeve 11 is in the closed position, a lower step surface of the switching limit step 112 is in contact with the switching control member 33, to limit the switching control member 33 in the lower position.

Furthermore, when the driving sleeve 11 is in the closed position, an end of the switching control member 33 further abuts against a lateral step surface of the switching limit step 112. An end, close to the end effector 4, of the driving sleeve 11 abuts against an end of a second elastic reset member. The other end of the second elastic reset member is relatively fastened to the handle housing 6. Relative fastening refers to that the two remain in a fastened relationship, but are not necessarily directly connected. The second elastic reset member in this embodiment is specifically a compression spring 8. With the arrangement of the second elastic reset member, after the end effector is closed, an abutting biasing force can be kept, so that the jaws are stably closed and are kept from being disengaged, and the driving sleeve 11 does not retract.

Furthermore, the switching control member 33 is further connected to a reset button. The reset button is at least partially located on an outer side of the handle housing 6. After the operation is completed, the reset button may be pressed to reset the apparatus. Alternatively, the reset button may be used when a fault occurs in the apparatus. In addition, the switching control member 33 is further connected with a third elastic reset member. The third elastic reset member is specifically a tension spring 9. Two ends of the tension spring 9 are respectively connected to the switching control member 33 and the handle housing 6. The switching control member 33 is L-shaped, and the middle portion is pivotally connected to the handle housing 6. Therefore, a section, in contact with the driving sleeve 11, of the switching control member 33 keeps a downward biasing force, so that when the driving sleeve 11 moves forward, the switching control member 33 can successfully enter the lower step surface of the switching limit step 112.

Figure 4:
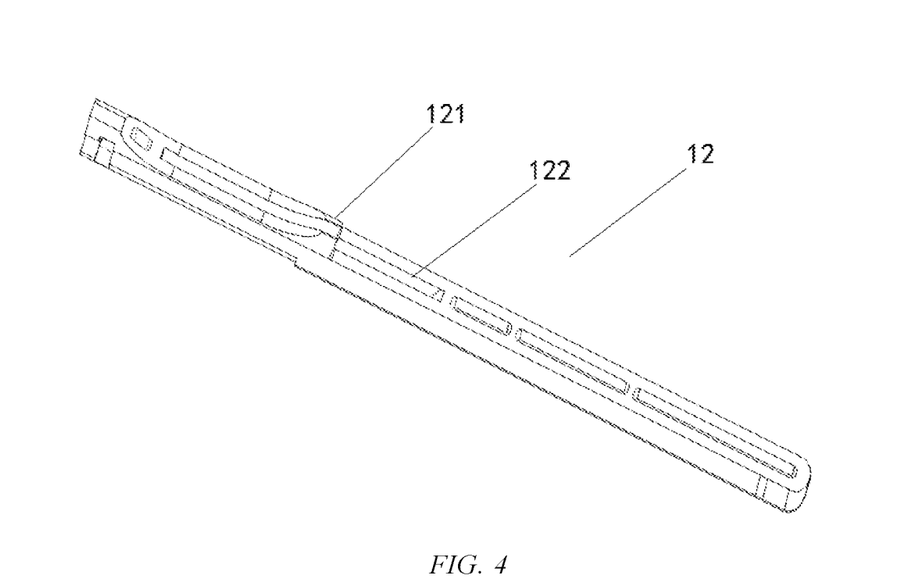
FIG. 4 is a schematic structural diagram of a knife bar driving rod according to an embodiment of this application.

Specifically, the knife bar driving rod 12 includes a pusher step 121 and a receding groove 122. The handle driving connecting member 32 passes through the receding groove 122 to be connected to the knife driving member 31. A width of the knife driving member 31 is greater than that of the receding groove 122. When the knife driving member 31 is in the driving position, the knife driving member 31 and the pusher step 121 of the knife bar driving rod 12 are engaged as the handle driving portion 21 moves toward the second position. A pusher step and a receding groove are disposed on a knife bar driving rod, so that space inside a handle housing of the stapling instrument can be effectively utilized, and the function of action switching can be accurately implemented without causing interference between parts.

Figure 6:
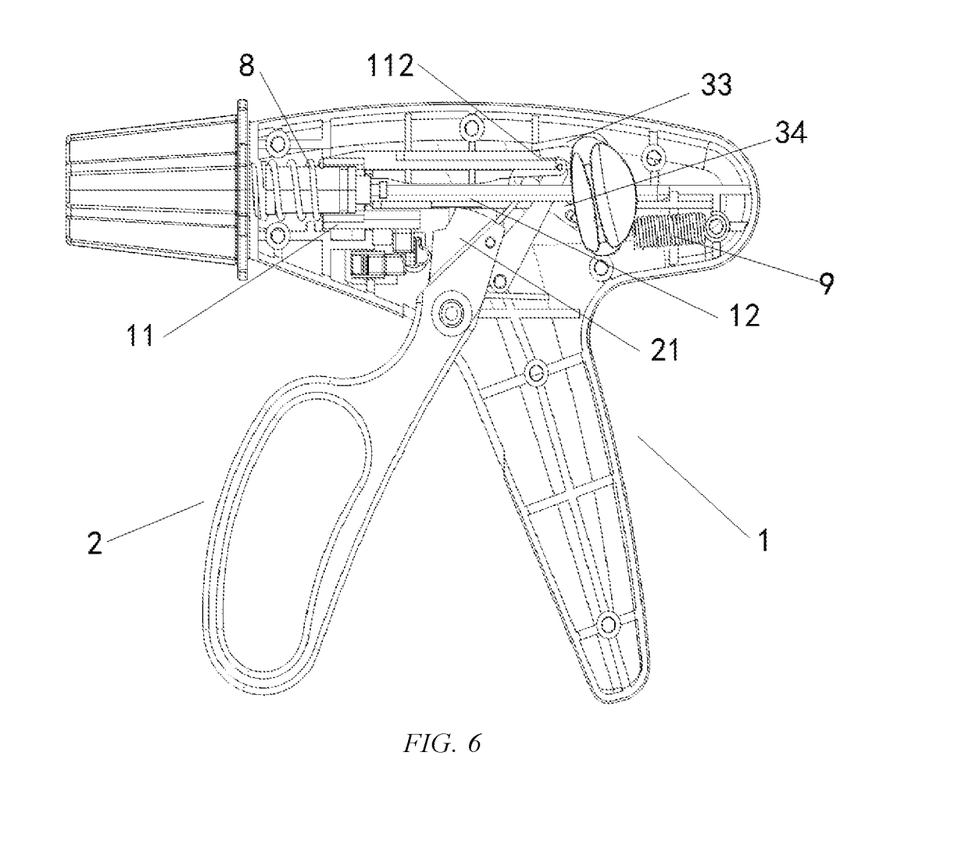
FIG. 6 is a partial schematic structural diagram of a stapling instrument in an initial state according to an embodiment of this application.
Figure 7:
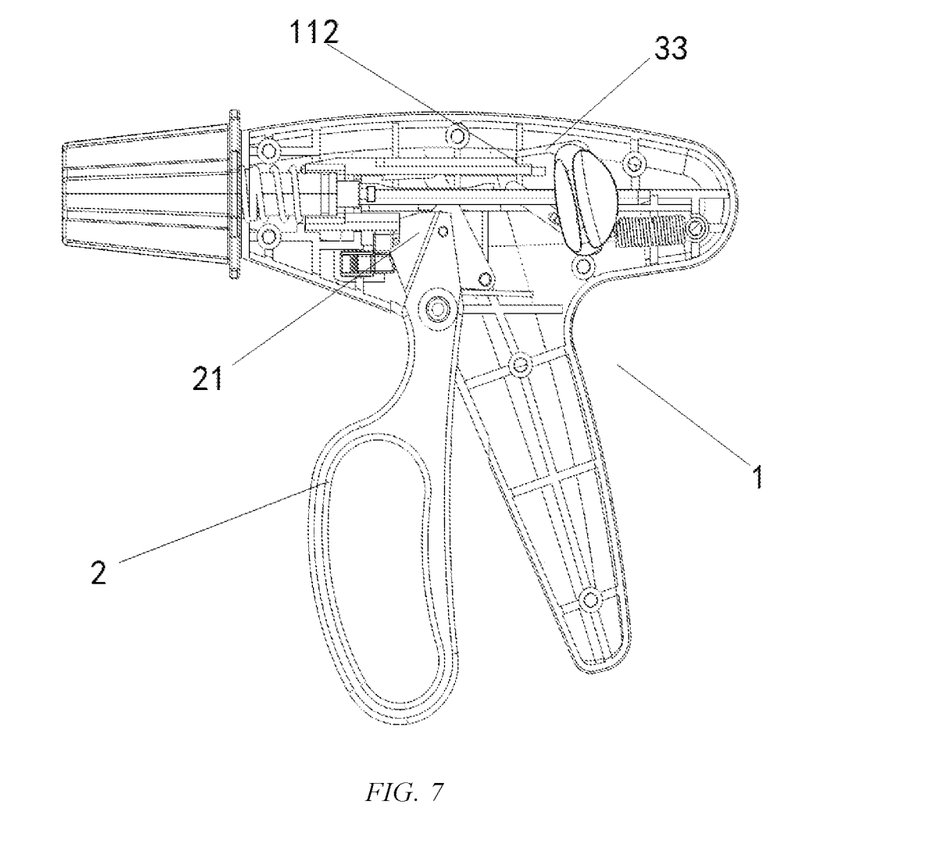
FIG. 7 is a partial schematic structural diagram of a stapling instrument during driving of gripping according to an embodiment of this application.

As can be known according to the foregoing embodiments, an operation process of this application is as follows:

First, as shown in FIG. 6, the stapling instrument is in the initial position. In this case, the driving handle 2 of the stapling instrument is pressed, so that the handle driving portion 21 moves from the first position at the proximal end to the second position at the distal end. The handle contact portion 111 of the driving sleeve 11 is pushed by the handle driving portion 21 to move toward a distal end, to drive the closing of the first gripping member 41 and the second gripping member 42. In this process, the switching limit step 112 moves toward the distal end along with the handle contact portion 111. An end of the switching control member 33 therefore enters the lower step surface from the upper step surface, as shown in FIG. 7.

Figure 8:
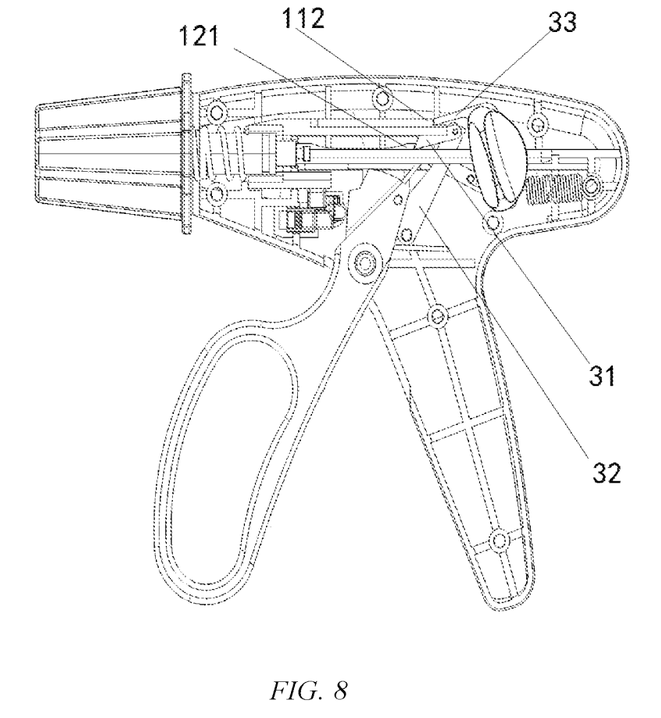
FIG. 8 is a schematic structural diagram showing that a handle is driven to return after gripping of an end effector according to an embodiment of this application.

After the driving handle 2 is reset, as shown in FIG. 8, the handle driving connecting member 32 passes through the receding groove 122 to be connected to the knife driving member 31. In this case, when the knife driving member 31 is in the driving position, the knife driving member 31 and the pusher step 121 of the knife bar driving rod 12 coincide in the same horizontal plane of the handle driving portion 21. The driving handle 2 is pressed, and the knife driving member 31 and the pusher step 121 of the knife bar driving rod 12 remain abutting against each other as the handle driving portion 21 moves toward the second position or are engaged in at least a part of the travel, to drive the knife bar driving rod 12 to move forward, to implement a stapling action.

As can be known according to the foregoing description, this application has the following advantages:

(1) A knife driving member with a switchable position only requires simple linkage coordination to perform different actions during handle driving.

(2) In coordination with a switching control member, operations of gripping and stapling can be successfully completed by repeatedly driving a handle without actively switching positions of the knife driving member.

(3) With a second elastic reset member, after a stapling instrument completes gripping, the stability of gripping can be kept without loosening.

(4) A pusher step and a receding groove are disposed on a knife bar driving rod, so that space inside a handle housing of the stapling instrument can be effectively utilized, and the function of action switching can be accurately implemented without causing interference between parts.

"An embodiment" or "embodiment" herein refers to specific features, structures or characteristics that can be included in at least one implementation of this application. In the description of this application, it should be understood that orientation or location relationships indicated by terms "up", "down", "top", and "bottom" are based on orientation or location relationships shown in the accompanying drawings, and are only used to facilitate description of this application and simplify description, but are not used to indicate or imply that the apparatuses or elements must have specific orientations or are constructed and operated at specific orientations, and therefore, cannot be understood as a limit to this application.

The foregoing provides description completely according to the object of the present invention. However, the present invention is not limited to the foregoing embodiments and implementations, and features in the embodiments may be combined with each other without causing any conflict. A person skilled in the art may make different changes and implementations within the scope allowed by the technical concept of the present invention.

What is claimed is:

1. A driving switching mechanism for a stapling instrument, the stapling instrument comprising an end effector (4) and a connecting tube (5), wherein the driving switching mechanism comprises an actuation driving assembly (1) and a handle driving assembly, and the actuation driving assembly (1) is at least partially provided inside the connecting tube (5);

the actuation driving assembly (1) comprises a driving sleeve (11) and a knife bar driving rod (12), the driving sleeve (11) is used for driving the end effector (4) to perform a closing action, and the knife bar driving rod (12) is used for driving the end effector (4) to perform a stapling action;

the handle driving assembly comprises a driving handle (2) and a knife bar driving assembly (3), the driving handle (2) comprises a handle driving portion (21), and the handle driving portion (21) is movable from a first position at a proximal end to a second position at a distal end; and the driving sleeve (11) is at least partially located on a movement path of the handle driving portion (21); and the knife bar driving assembly (3) comprises a knife driving member (31) and a handle driving connecting member (32), the handle driving connecting member (32) is connected to the handle driving portion (21), and the knife driving member (31) is movably connected to the handle driving connecting member (32), and is movable relative to the handle driving connecting member (32) to a driving position or a driving disengagement position; and when the knife driving member (31) is in the driving position, the knife driving member (31) and the knife bar driving rod (12) are engaged during the handle driving portion (21) moving toward the second position, wherein the knife bar driving assembly (3) further comprises a switching control member (33) and a knife limit member (34), the switching control member (33) is rotatably connected to a handle housing (6), the knife limit member (34) is synchronously rotatably connected to the switching control member (33), when the switching control member (33) is in an upper position, the knife limit member (34) abuts against and limits the knife driving member (31) in the driving disengagement position, and when the switching control member (33) is in a lower position, the knife driving member (31) is not limited by the knife limit member (34) in the driving position.

2. The driving switching mechanism for stapling instrument according to claim 1, wherein the driving handle (2) further comprises a handle holding portion (23) and a handle hinge portion (24), and the driving handle (2) is rotatably connected to a handle housing (6) by the handle hinge portion (24).

3. The driving switching mechanism for stapling instrument according to claim 2, wherein the driving handle (2) and the handle housing (6) are provided with a first elastic reset member.

4. The driving switching mechanism for stapling instrument according to claim 1, wherein the driving sleeve (11) comprises a handle contact portion (111) and a switching limit step (112); and the handle driving portion (21) pushes the driving sleeve (11) from an initial position to a closed position by pushing the handle contact portion (111);

when the driving sleeve (11) is in the initial position, an upper step surface of the switching limit step (112) is in contact with the switching control member (33), to limit the switching control member (33) in the upper position; and when the driving sleeve (11) is in the closed position, a lower step surface of the switching limit step (112) is in contact with the switching control member (33), to limit the switching control member (33) in the lower position.

5. The driving switching mechanism for stapling instrument according to claim 4, wherein when the driving sleeve (11) is in the closed position, an end of the switching control member (33) further abuts against a lateral step surface of the switching limit step (112).

6. The driving switching mechanism for stapling instrument according to claim 5, wherein an end, close to the end effector (4), of the driving sleeve (11) abuts against an end of a second elastic reset member, and the other end of the second elastic reset member is relatively fastened to the handle housing (6).

7. The driving switching mechanism for stapling instrument according to claim 5, wherein the switching control member (33) is further connected to a reset button, and the reset button is at least partially located on an outer side of the handle housing (6).

8. The driving switching mechanism for stapling instrument according to claim 1, wherein the knife bar driving rod (12) comprises a pusher step (121) and a receding groove (122), the handle driving connecting member (32) passes through the receding groove (122) to be connected to the knife driving member (31), a width of the knife driving member (31) is greater than that of the receding groove (122), and when the knife driving member (31) is in the driving position, the knife driving member (31) and the pusher step (121) of the knife bar driving rod (12) are engaged during the handle driving portion (21) moving toward the second position.

9. A stapling instrument, comprising an end effector (4), a connecting tube (5), and the driving switching mechanism according to claim 1.

* * * * *